United States Patent [19]

Roux

[11] E Patent Number: Re. 31,865

[45] Reissued Date of Patent: Apr. 16, 1985

[54] ARTIFICIAL JOINTS, IN PARTICULAR COXO-FEMORAL JOINTS

[76] Inventor: Christiane Roux, Noisy sur Ecole, 77123 Le Vaudoue, Seine-et-Marne, France

[21] Appl. No.: 486,037

[22] Filed: Apr. 18, 1983

Related U.S. Patent Documents

Reissue of:

[64] Patent No.: 4,262,369
Issued: Apr. 21, 1981
Appl. No.: 49,905
Filed: Jun. 19, 1979

[30] Foreign Application Priority Data

Jun. 21, 1978 [FR] France ..... 78 18619

[51] Int. Cl.[3] ..... A61F 1/03

[52] U.S. Cl. ..... 3/1.912; 3/1.9; 128/92 CA

[58] Field of Search ..... 3/1.9, 1.91, 1.911, 3/1.912, 1.913; 128/92 C, 92 CA

[56] References Cited

U.S. PATENT DOCUMENTS

| | | | |
|---|---|---|---|
| Re. 28,895 | 7/1976 | Noiles | 3/1.912 |
| 3,579,831 | 5/1971 | Stevens et al. | 433/174 |
| 3,818,512 | 6/1974 | Shersher | 3/1.912 |
| 3,820,167 | 6/1974 | Sivash | 3/1.912 |
| 3,894,297 | 7/1975 | Mittelmeier et al. | 128/92 CA X |
| 3,943,576 | 3/1976 | Sivash | 3/1.912 X |
| 4,126,924 | 11/1978 | Akins et al. | 3/1.912 X |

FOREIGN PATENT DOCUMENTS

| | | | |
|---|---|---|---|
| 2247721 | 4/1974 | Fed. Rep. of Germany | 3/1.912 |
| 2628443 | 12/1976 | Fed. Rep. of Germany | 3/1.9 |
| 2096895 | 3/1972 | France | 3/1.912 |
| 2183231 | 12/1973 | France | 3/1.912 |
| 2183232 | 12/1973 | France | 3/1.912 |
| 2183233 | 12/1973 | France | 3/1.912 |
| 2297030 | 9/1977 | France | 3/1.912 |
| 2295729 | 4/1979 | France | 3/1.912 |

*Primary Examiner*—Clifford D. Crowder
*Attorney, Agent, or Firm*—Diller, Ramik & Wight

[57] ABSTRACT

A joint prosthesis and particularly for the coxo-femoral or hip joint, said prosthesis being formed by an inner cupule and an outer ring. The outer ring, which is made of metal, is shrunk on the inner cupule, which is made of a ceramic or monocrystalline material. An intermediate annular piece may be provided between the cupule and the outer ring. Preferably the outer ring is provided with an external self-tapping thread.

24 Claims, 7 Drawing Figures

ARTIFICIAL JOINTS, IN PARTICULAR COXO-FEMORAL JOINTS

Matter enclosed in heavy brackets [ ] appears in the original patent but forms no part of this reissue specification; matter printed in italics indicates the additions made by reissue.

FIELD OF THE INVENTION

The present invention generally relates to artificial joints, and in particular coxo-femoral or hip joints, and relates more specifically to that part of these joints, hereinafter called articular prosthesis, comprising a substantially hemispherical cotyloid cavity adapted to cooperate, in the manner of a ball joint, with a spheroid head.

BACKGROUND OF THE INVENTION

Such an articular prosthesis is to be implanted in a cavity made to this end in the bone concerned, the hip bone when a coxo-femoral joint is in question.

It must therefore comply with a double imperative: on the one hand, its outer surface must be provided with means adapted to allow a firm implantation thereof in the corresponding osseous cavity and, on the other hand, it must present, inside, at cotyloid cavity level, good surface and mechanical resistance qualities suitable for a cooperation, without noteworthy friction and without too rapid wear, with the spheroid head with which it is associated.

The implantation of this articular prosthesis may be effected, at the present time, by sealing or embedding or by screwing.

In the case of an implantation by sealing or embedding, it is preferable, for a better fixing in the osseous cavity concerned, if the articular prothesis in question has a rough outer surface, for example a porous macroscopic roughness outwardly open by pores, promoting growth and consolidation of the bone, as is the case of so-called "madreporic" cotyloid prostheses.

In the case of an implantation by screwing, it is obviously necessary that the articular prosthesis in question has at least one outer helical thread, as is the case in particular in French patent application filed on Feb. 27, 1974 under No. 74 42974 and published under No. 2,295,729, this helical thread furthermore being, in certain cases, self-tapping.

In view of the surface and mechanical resistance qualities that an articular prosthesis must have at cotyloid cavity level, this articular prosthesis is presently most often made of synthetic material, for example polyethylene, and even irradiated polyethylene, but it has been proposed to make them of ceramics, for example fritted alumina ceramics, as is the case in particular in French patent filed July 10, 1970 under No. 70 25848 and published under No. 2,096,895, to use the inherent qualities, known for a long time, of such a material.

In fact, ceramic materials, and this is also the case of monocrystalline materials, present, with respect to conventional metallic materials, incomparable advantages of considerable hardness, reduced coefficient of friction, inalterability, biological compatibility with the osseous tissues, and compressive strength.

On the other hand, due to their relatively low resilience and tensile strength, they are fragile to shocks.

In addition, they are not easy to machine and, in particular, it is difficult to make surface roughness or screw threads thereon.

The articular prostheses of the type in question are at the present time most often made in one piece.

For the above reasons, it is in practice difficult to give them a rough surface or threads when they are made of ceramics.

It has been proposed to form such an articular prosthesis with the aid of two separate parts, namely an inner cupule made of synthetic material, and an outer cupule made of metal, as is the case in particular in French patent filed on Jan. 7, 1975 under No. 75 00356 and published under No. 2,297,030, for an articular prosthesis to be implanted by sealing or embedding, and a similar arrangement has been adopted for articular prostheses to be screwed, the screw thread thus being formed on a less fragile metal part, namely an outer ring, and the cotyloid cavity on a part made of a material having better qualities of friction than metal, namely an inner cupule made of synthetic material.

However, in both cases, the inner cupule is made of a synthetic material, i.e. a material having surface and mechanical resistance qualities which are inferior to those of a ceramic material or a monocrystalline material and furthermore unlike the latter, capable of an untimely creep, due to the appreciable elasticity that it presents.

In addition, in both cases, the positioning of the articular prostheses in question does not include any disposition for promoting a rapid regeneration of the osseous tissue in which they are implanted.

SUMMARY OF THE INVENTION

It is a general object of the present invention to provide an articular prosthesis for an artificial joint which is such as to allow the use of a ceramic material or a monocrystalline material for constituting its cotyloid cavity, whilst allowing its outer surface to be readily provided with any profile or relief, for example surface roughness or screw threads, deemed necessary to ensure a good fixing thereof in the osseous cavity in question, and/or for promoting the consolidation of the tissue thereof.

The articular prosthesis according to the invention which, according to a first aspect, is of the type comprising two separate parts, namely an inner cupule and an outer ring, is, according to this aspect, characterized in that said cupule is subjected to an annular shrinking stress, or hooping action, which is applied thereto by the outer ring, either directly, or indirectly by means of an intermediate annular piece between said cupule and said outer ring.

The shrinking stress thus applied to the inner cupule is easy to calculate as a function of the desired effects, and is advantagously reproducible from one prosthesis to another.

In addition, it is compatible with the production of the inner cupule of such prosthesis made of ceramic material of monocrystalline material, this not being the case, for the reasons of creep mentioned hereinabove, if it were made of synthetic material, which is always more or less elastic.

Jointly, the surface roughness possibly to be provided may easily be effected, the outer ring, independently of the inner cupule, being made of a metal chosen both for its possibilities of machining and for its capacity to develop elastically, i.e. without permanent deformation, the shrinking stress to be ensured.

Moreover, the shrinking according to the invention advantageously enables any glue or other adhesive product for connecting the inner cupule to the outer ring, to be dispensed with, and therefore the consequences of a possible ageing by use of such a product, to be avoided.

In practice, the inner cupule may advantageously be made of any ceramic material, for example fritted metal oxide, such as alumina, zirconium oxide, titanium oxide or the like, or of any monocrystalline material, for example alumina in the form of sapphire or ruby, or carbon, whilst the outer ring is for example made of titanium, titanium alloy, or any other metal or metal alloy comprising for example chromium and/or nickel, and/or cobalt.

As mentioned hereinabove, the outer ring may have an outer rough surface, for example of the madreporic type.

As a variant, the outer ring may be provided with at least one outer helical screw thread, for example a self-tapping thread.

In such a case, and according to a possible development of the invention, the articular prosthesis according to the invention may comprise an inner collecting volume, opening to the outside, in places via openings, in line with said self-tapping thread, which volume is thus adapted to receive bone chips.

Thus, according to the invention, arrangements are made in this case to conserve all chips of bone detached by the self-tapping thread of the articular prosthesis concerned when it is placed in position, such bone chips being such as to locally form germs for osseous regeneration accelerating by osteogenesis, the reconstitution of the wall of the osseous cavity in which this articular prosthesis is implanted.

In addition, through the openings by which the inner collecting volume that this articular prosthesis thus comprises, communicates with the outside, there is, according to the invention, a progressive interpenetration of this prosthesis and the bone in which it is implanted, as this bone regenerates, thus ensuring a particularly efficient anchoring of this prosthesis in the bone.

These arrangements being interesting per se, the present invention further relates, according to a second aspect, to an articular prosthesis, of the type comprising, on the inside, a substantially hemispherical cotyloid cavity and, on the outside, projecting therefrom, at least one self-tapping helical thread, this articular prosthesis being characterized in that it comprises, internally, a collecting volume, which opens to the outside, in places, via openings, in line with the said self-tapping thread, and which is thus adapted to receive bone chips, whether or not this articular prosthesis is made in two distinct parts although such a production in two distinct parts is preferred as being advantageous favourable to closing off such a collecting volume.

However, the production of such an articular prosthesis in two distinct parts may also, if desired, and according to another aspect of the invention, be profitably used for the insertion, between the inner cupule and the outer ring constituting these parts, of a tubular sleeve made of elastic material forming a damping member.

Such a damping member is favourable to the user's comfort and to the protection and long life of the other members which are in connection with the joint in question.

The invention will be more readily understood on reading the following description with reference to the accompanying drawings.

DETAILED DESCRIPTION OF THE PREFERRED EMBODIMENTS

Figure 1:
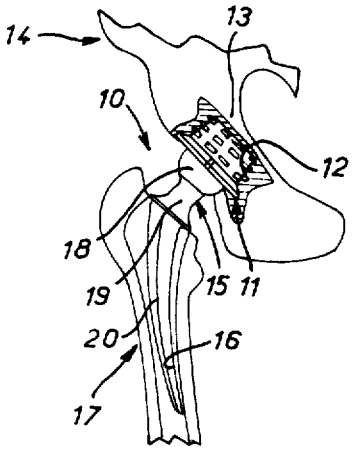
FIG. 1 is an overall view in elevation of an artificial coxo-femoral joint comprising a cotyloid prosthesis according to the invention.

Referring now to the drawings, FIG. 1 shows an artificial coxo-femoral joint generally referenced 10.

This coxo-femoral joint comprises, in manner known per se, a so-called cotyloid articular prosthesis 11, implanted in a cavity 12 made in the coxal part 13 of the hip bone 14 of the patient, and a femoral prosthesis 15, implanted in a cavity 16 made in the patient's femur 17.

Figure 5:
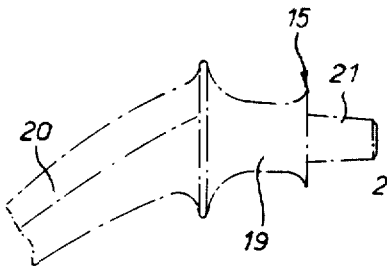
Figure 5:
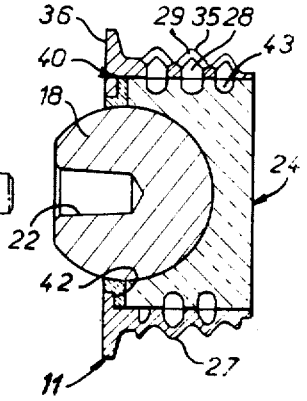

The femoral prosthesis 15 comprises, in manner known per se, a spheroid head 18 at the end of a neck 19 integral with a pin 20 engaged in the corresponding osseous cavity 16; for example, and as may be seen in particular in FIG. 5, the spheriod head 18 may constitute a part distinct from the rest of the femoral prosthesis 15 to which it belongs, this head therefore being able to be made of ceramic material, whilst the rest of said prosthesis is made of metal.

Likewise by way of example, as is shown in broken lines in FIG. 5, the connection of the spheroid head 18 with the neck 19 associated therewith may be effected by a conical coupling, this neck 19 having a truncated endpiece 21 projecting therefrom, on which the spheriod head 18, which, to this end, has a complementary truncated inner bore 22, may be forcibly engaged.

As these arrangements are wall known per se and do not form part of the present invention, they will not be described in greater detail here.

The cotyloid prosthesis 11 according to the invention comprises, likewise in manner known per se, two distinct parts, namely an inner cupule 24 inside which a substantially hemispherical cotyloid cavity 25 is hollowed, and an outer ring 26 having projections on its outer surface.

In the examples of application of the invention illustrated by FIGS. 1 to 5, these projections are constituted by a self-tapping thread 27.

Figure 2:
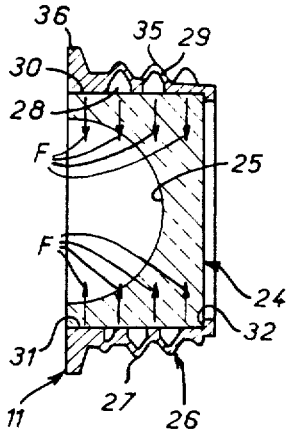
FIG. 2 is, on a larger scale, a view in axial section through this cotyloid prosthesis, along the broken line II—II of FIG. 3.
Figure 3:
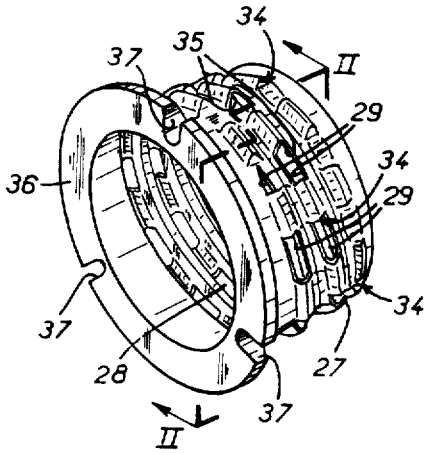
FIG. 3 is, on a different scale, a view in elevation of the single outer ring of this cotyloid prosthesis.

According to the invention, the inner cupule 24 is subjected to hooping action or an annular shrinking stress which is applied thereto by the outer ring 26, in the direction of arrows F or FIG. 2, and, in the embodiment of this FIG. 2, this hooping action or shrinking stress is transmitted directly from the outer ring 26 to the inner cupule 24, the inner cupule 24 being directly in contact with the outer ring 26 and having, to this end, a cylindrical outer surface 30 complementary of the inner bore 31 of the outer ring 26.

At its axial end opposite the inner cupule 24, the outer ring 26 internally presents, in this case, a transverse support shoulder 32.

As mentioned hereinabove, the inner cupule 24 may be made of any ceramic or monocrystalline material, and the outer ring 26 of any metal.

The hooping or shrinking to be ensured is effected for example by slight heating of the outer ring 26 before it is engaged on the inner cupule 24, this heating being conducted so as to take the outer ring 26 to a temperature at least equal to that which the inner cupule 24 will have to withstand in the course of the sterilization process to which the whole will then be subjected, and for example to a temperature similar thereto. This may be of about 200° C.

A high frequency heating may be suitable, and it should be noted that, if desired, such a heating may also, in reverse, allow a disconnection of the outer ring 26 from the inner cupule 24, without any damage to one or the other of these parts.

During the shrinking or hooping operation, the inner cupule may remain at ambient temperature.

According to the invention, in the embodiments illustrated in FIGS. 1 to 5, the cotyloid prosthesis 11 further comprises an inner collecting volume 28 which opens to the outside in places via openings 29, in line with the self-tapping thread 27, and which is adapted to receive bone chips.

In the embodiment shown in FIG. 2, the inner volume 28 according to the invention is internally confined partly by the inner cupule 24, and partly by the outer ring 26.

In practice, and as is shown, this inner volume 28 is formed by a helical groove which, inside the outer ring 26, forms a hollow which is complementary to or replica of the self-tapping thread 27, said groove following the contour of said thread and being arranged in the thickness thereof.

The self-tapping thread 27 being intersected axially by notches 34 intended, according to a conventional technique in this field, to render it self-tapping, the openings 29 through which the inner volume 28 according to the invention opens to the outside, are established at the intersections of this self-tapping thread 27 and these notches 34.

The self-tapping thread 27 may have any cross-section, for example a substantially isosceles triangle, as shown.

This thread being hollow, at least certain of the sections which define the notches 34 form triangular recesses 35 in continuity with the corresponding openings 29.

The opening of these triangular recesses may be tapered, to accentuate the self-tapping character of the thread 27.

On the cotyloid cavity 25 side of the inner cupule 24, the outer ring 26 forms at its axial end a support flange 36 which projects radially outwardly.

In this support flange 36 are arranged from place to place holes or notches 37 adapted to allow the outer ring 26 to mesh with any drive tool provided to this end with claws complementary of these holes or notches 37.

As will be readily understood, after a suitable arrangement of the osseous cavity 12, by drilling, the outer ring 24, provided with the inner cupule 24, is screwed in this cavity, and the corresponding screwing operation is advantageously facilitated by the self-tapping nature of this outer ring 26.

The cotyloid prosthesis 11 thus positioned is therefore ready to cooperate with a femoral prosthesis 15.

Figure 4:
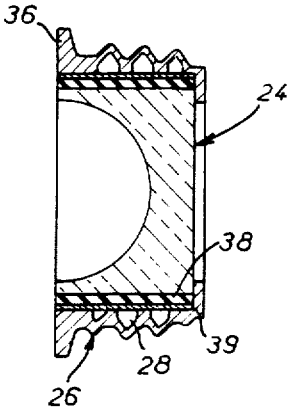
FIGS. 4 to [6] 7 are views similar to that of FIG. 2 and each respectively concerns an alternative embodiment.

According to the alternative embodiment illustrated in FIG. 4, the outer ring 26 is internally lined with a tubular sleeve 38 made of elastic material; a tubular jacket 39, made of rigid materal, for example metal, is preferably provided between the said sleeve and the outer ring 26, as shown, to avoid a creeping of this sleeve in the inner volume 28 according to the invention.

The jacket 39 may be welded or brazed to the outer ring 26, or the corresponding connection may be ensured by shrinking, as before.

The tubular sleeve 38 made of elastic material may be connected to the jacket 39 by gluing, or by simple force-fitting; the connection to the inner cupule 24 may be effected in similar manner.

In all cases, such a sleeve 38 made of elastic material totally transmits to the inner cupule 24 the shrinking stress developed by the outer ring 26, an elastic material being, as is known, incompressible.

In the alternative embodiment illustrated in FIG. 5, at the axial end of the outer ring 26 located on the inner cupule 24 side, there is disposed a retaining ring 40, of which the inner periphery prolongs the cotyloid cavity 25, slightly closing said latter, to retain the spheroid head 18, the latter thus being mounted as a ball joint between the inner cupule 24 and the retention ring 40, without risk of dislocation.

The positioning, in the outer ring 26, of the retaining ring 40, the spheroid head 18 and the inner cupule 24 is effected, in this case, by the axial end of this ring opposite the cotyloid cavity 25 of this cupule, and the retaining ring 40 abuts on a transverse shoulder 42 of the outer ring 26.

Furthermore, in this alternative embodiment, and according to a feature applicable to the other alternative embodiments, the inner collecting volume 28 according to the invention comprises, opposite the helical groove made in the outer ring 26, as described hereinabove, a similar helical groove 43, made on the surface of the inner cupule 24.

For this alternative embodiment, the fitting of the truncated endpiece 21 on the spheroid head 18 is of course effected after the cotyloid prosthesis has been positioned in the hip bone 14.

Figure 6:
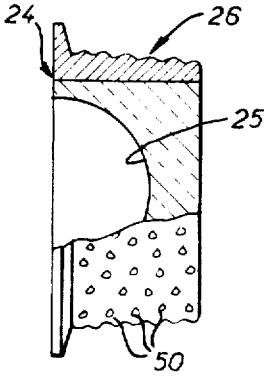

FIG. 6 illustrates the application of the invention to a cotyloid prosthesis to be positioned not by screwing, as before, but by sealing or embedding.

Figure 7:
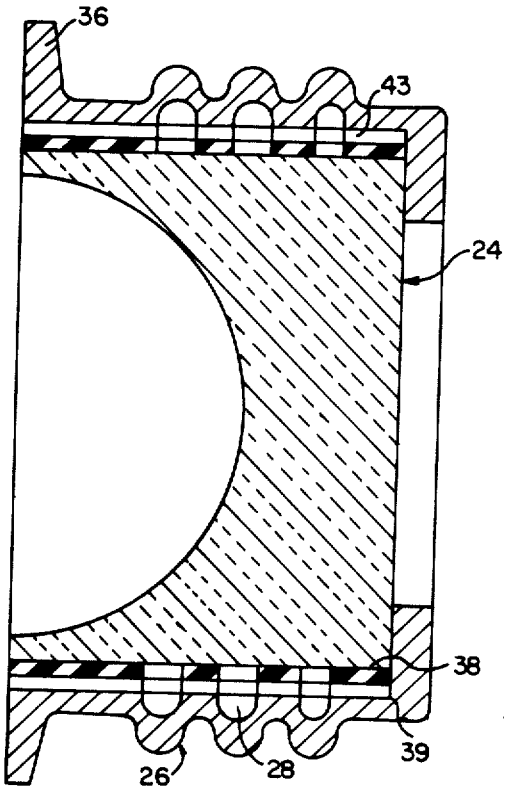

*Another alternative embodiment of the femoral prosthesis is illustrated in FIG. 7. This embodiment is the same as that of FIG. 4 except that there is provided a helical groove 43', similar to that formed in the outer ring 26, as described above, formed in the tubular sleeve 38.*

As shown, the surface of the outer ring 26 is preferably rough; for example, and as has been schematically shown, the roughness is in the form of individual madreporic type islands 50.

However, other types of roughness may be envisaged.

The present invention is not limited to the embodiments which have been described and shown, but covers all alternatives and/or combination thereof, particularly concerning the elastic sleeve of the embodiment illustrated in FIG. 4 which could also be used in the embodiment illustrated in FIG. 5 or that illustrated in FIG. 6.

In the case of a prosthesis to be screwed, a plurality of screw threads may be provided.

In addition, although the invention is quite naturally applicable to the case of articular prostheses made in two distinct parts, the formation of the inner collecting volume which characterizes it being facilitated thereby, it may also be applied in the case of articular prostheses in one piece.

Finally, the aplication of this invention is not limited too the coxo-femoral joints, but also extends to other joints, for example to the scapulo-humeral joints.

What is claimed is:

1. An articular prosthesis for an artificial joint, comprising two separate parts including an inner cupule and an outer ring, said inner cupule having a part spherical cavity adapted to receive a corresponding part spherical head, said inner cupule being made of a hard and rigid material of low tensile strength and shock resistance, said outer ring being made of metal, said outer ring being shrunk fit on the sidewall of inner cupule.

2. The prosthesis of claim 1, said outer ring having at least one external self-tapping thread, wherein said outer ring has discrete openings communicating with at least one internal volume for collecting bone chips resulting from tapping said outer ring in bone tissue.

3. The prosthesis of claim 2, further comprising axial notches intersecting said self-tapping thread, said openings in said outer ring being disposed at the intersections of said thread and said notches.

4. The prosthesis of claim 2, wherein said inner volume is confined partly by said inner cupule and partly by said outer ring.

5. The prosthesis of claim 2, wherein an intermediate annular piece is disposed between said inner cupule and said outer ring, said inner volume being confined partly by said intermediately annular piece and partly by said outer ring.

6. The prosthesis of claim 1, further comprising a retaining ring for retaining a spherical head of complementary configuration in said part spherical cavity of said inner cupule.

7. The prosthesis of claim 6, further comprising a transverse shoulder on the inner side of said outer ring adjoining the open end of said part spherical cavity, said retaining ring abutting against said transverse shoulder.

8. The prosthesis of claim 1, further comprising a tubular sleeve of elastic material internally lining said outer ring.

9. The prosthesis of claim 8, further comprising a tubular jacket of rigid material provided between said outer ring and said tubular sleeve whereby said tubular sleeve is confined between said tubular jacket and said sidewall of said cupule.

10. The prosthesis of claim 1, wherein said inner cupule is made of ceramic material.

11. The prosthesis of claim 1, wherein said inner cupule is made of monocrystalline material.

12. The prosthesis of claim 1, wherein said sidewall of said inner cupule is defined by a body of revolution having a straight line generatrix.

13. The prosthesis of claim 1, wherein means on the outer surface of said outer ring is adapted to be embedded in a bone tissue.

14. An articular prosthesis for an artificial joint comprising two distinct parts, as inner cupule and an outer ring, said outer ring [being shrunk fit on] *receiving* said inner cupule, said outer ring being provided with at least one external self-tapping thread, and with an inner collecting volume which opens to the outside, in places, through openings, in line with said self-tapping thread and which is adpated to receive [bond] *bone* chips, said inner volume being partly comprised by a helical groove which forms a hollow complementary to said self-tapping thread, said groove following the contour of said thread and being at least partly formed in the thickness thereof.

15. The prosthesis of claim 14, wherein said inner volume is confined between said inner cupule and said outer ring, said inner volume being partly defined opposite said helical groove in said outer ring by a similar helical groove in the surface of said inner cupule.

16. The prosthesis of claim 14, wherein a tubular sleeve overlies the sidewall of said inner cupule, said inner volume between said tubular sleeve and said outer ring, said inner volume being partly defined opposite said helical groove in said outer ring by a similar helical groove in said tubular sleeve opposite said helical groove in said outer ring.

*17. The prosthesis of claim 14, wherein the outer ring is internally lined by a tubular jacket, said collecting volume being formed between said outer ring and said tubular jacket.*

*18. An articular prosthesis for an artificial joint comprising two distinct parts, including an inner cupule and an outer ring, said inner cupule being received on said outer ring, said outer ring being provided with at least one external self-tapping thread, and with an inner collecting volume, which is at least partly formed within the inner volume of the said outer ring, radially between said outer ring and said inner cupule, and which opens to the outside, at spaced locations, through openings in said self-tapping thread, said collecting volume being adapted to receive bond chips.*

*19. The prosthesis of claim 18, wherein the outer ring is internally lined by a tubular jacket, said collecting volume being formed between said outer ring and said tubular jacket.*

*20. An articular prosthesis for an artificial joint comprising two distinct parts, including an inner cupule and an outer ring, said inner cupule being received on said outer ring, said outer ring being provided with at least one external self-tapping thread, and with an inner collecting volume, which is at least partly formed within the inner volume of the said outer ring, between said outer ring and said inner cupule, and which opens to the outside, at spaced locations, through openings in said self-tapping thread, said collecting volume extending circumferentially in at least one direction from said openings and being adapted to receive bone chips.*

*21. The prosthesis of claim 20, wherein the outer ring is internally lined by a tubular jacket, said collecting volume being formed between said outer ring and said tubular jacket.*

*22. An articular prosthesis for an artificial joint comprising two distinct parts, including an inner cupule and an outer ring, said inner cupule being received on said outer ring, said outer ring being provided with at least one external self-tapping thread, and with an inner collecting volume, which is at least partly formed by a hollow defined along the inner surface of said outer ring, between said outer ring and said inner cupule, and which opens to the outside, at spaced locations, through openings in said self-tapping thread, said collecting volume being adapted to receive bone chips.*

*23. The prosthesis of claim 22, wherein the outer ring is internally lined by a tubular jacket, said collecting volume*

*being formed between said outer ring and said tubular jacket.*

*24. An articular prosthesis for an artificial joint comprising two distinct parts, including an inner cupule and an outer ring, said inner cupule being received on said outer ring, said outer ring being provided with at least one external self-tapping thread, and with an inner collecting volume, which is at least partly formed within the inner volume of said outer ring, between said outer ring and said inner cupule, and which opens to the outside, at spaced locations, through openings in said self-tapping thread, said collecting volume being adapted to receive bone chips, the outer ring internally comprises a helical groove which forms a hollow complementary to said self-tapping thread, said groove following the contour of said thread and being at least partly formed in the thickness thereof, said collecting volume being at least partly formed by said helical groove.*

* * * * *